Figure 1:
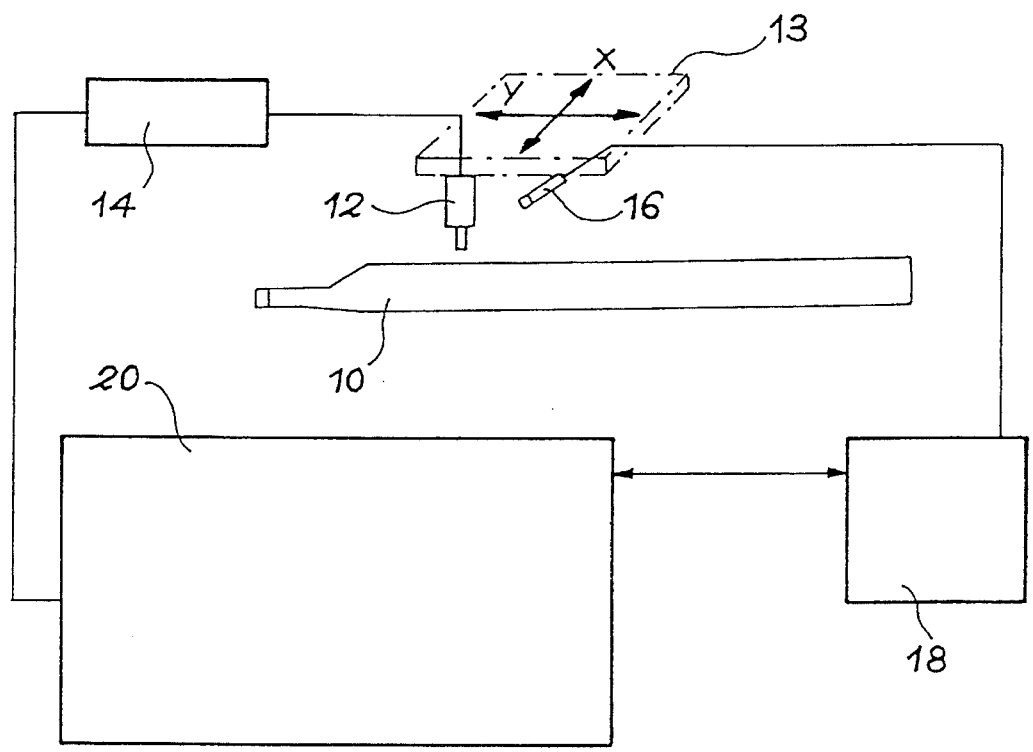

United States Patent [19]

Baudrillard et al.

[11] Patent Number: 5,589,635
[45] Date of Patent: Dec. 31, 1996

[54] AUTOMATED TAPPING PROCESS FOR COMPLEX PARTS USED FOR DETECTING SHALLOW FAULTS

[75] Inventors: Gilles Baudrillard, Suresnes; Christophe P. Bouju, Paris, both of France

[73] Assignee: Aerospatiale Societe Nationale Industrielle, France

[21] Appl. No.: 512,531

[22] Filed: Aug. 8, 1995

[30] Foreign Application Priority Data

Aug. 8, 1994 [FR] France .................................. 94 09808

[51] Int. Cl.$^6$ ............................................. G01N 9/24
[52] U.S. Cl. ................................. 73/600; 73/602
[58] Field of Search ........................... 73/583, 598, 600, 73/602, 620, 649

[56] References Cited

U.S. PATENT DOCUMENTS

| | | | |
|---|---|---|---|
| 4,475,399 | 10/1984 | Livingston | 73/622 |
| 4,881,405 | 11/1989 | Paquet | 73/146 |
| 5,309,765 | 5/1994 | Horigome et al. | 73/602 |
| 5,331,855 | 7/1994 | Takashita et al. | 73/602 |
| 5,383,366 | 1/1995 | Wallingford et al. | 73/602 |

FOREIGN PATENT DOCUMENTS

| | | |
|---|---|---|
| 4207728 | 9/1993 | Germany . |
| 8707378 | 12/1987 | WIPO . |
| 9212423 | 7/1992 | WIPO . |

OTHER PUBLICATIONS

Windsor, Colin G.; The Classification of Defects From Ultrasonic Measurements; Neutral Networks from Models to Applications; Paris, France 1988; pp. 592–601.

Damarla, T. R. and Zhao, Wei Ning; A Learning Algorithm for a CMAC–based System and its Application for Classification of Ultrasonic Signals; Ultrasonics, vol. 32, No. 2, Mar. 1994; pp. 91–98.

*Primary Examiner*—Richard Chilcot
*Assistant Examiner*—Max Noori
*Attorney, Agent, or Firm*—Dvorak and Traub

[57] ABSTRACT

In order to carry out the automated tapping of complex parts 10, such as helicopter blades, the surface to be inspected is subject to successive shocks using an impacting head 12 displaced in accordance with a given spacing or pitch. The sound produced by these shocks are collected by a microphone 16 associated with an acquisition circuit 18. At least two successive sound signals, which may or may not be consecutive, are compared in order to establish a fault diagnosis. The comparison and diagnosis are carried out by a neuron network or system, after the number of representative points of each sound signal has been reduced during a preprocessing involving a selection stage followed by a smoothing stage.

12 Claims, 4 Drawing Sheets

AUTOMATED TAPPING PROCESS FOR COMPLEX PARTS USED FOR DETECTING SHALLOW FAULTS

DESCRIPTION

The invention relates to a process making it possible to inspect or test complex parts in automated manner using the acoustic response produced by successive shocks applied in the form of impacts distributed over a surface of the part which is to be tested.

This process can be used for performing a non-destructive inspection or testing of composite, metallic and similar material parts having random shapes and sizes, to the extent that said parts have a complex structure and e.g. a surface coating fixed by adhesion to a support. The use of the process according to the invention is particularly advantageous in the case of parts having very complex structures such as the blades of rotary-wing aircraft. It makes it possible to detect shallow faults and defects (down to approximately 4 mm), such as peeling, separation and homogeneity faults in structures.

There are numerous non-destructive testing methods. Thus, reference is made in non-limitative manner to ultrasonic inspection, holography, radioscopy, radiography, dimensional checks, etc.

When the structures of the parts are very complex and in particular when there are different materials e.g. assembled by adhesion or bonding in the thickness direction, it may be necessary to use in combination several complementary checking or inspection methods. This observation more particularly relates to safety-essential parts, such as the blades of rotary-wing aircraft, in which it is vital to detect the presence of a fault.

In the case of the inspection of very complex structures such as the blades of rotary-wing aircraft, the various non-destructive testing methods conventionally used include tapping. Tapping serves to detect any shallow faults (down to approximately 4 mm), such as the separation or peeling of surface coatings or the presence of non-homogeneous surface areas. It consists of applying to the part successive shocks, whose impacts are distributed over the surface to be inspected. The sound produced by these shocks, i.e. the acoustic response induced by them in the part, enable the inspector to detect possible faults and produce the cartography thereof on the part.

At present no automated inspection machine exists able to carry out tapping or an inspection able to detect the same type of fault on parts having comparable structures. Thus, although an apparatus exists making it possible to apply successive shocks to a part, such as that illustrated by FR-A-2,062,069, the inspector remains completely responsible for producing the diagnosis.

Therefore the reliability of the tapping is therefore essentially dependent on the quality of the training of the inspector. It cannot therefore be separated from the human factor and can lead to methods or reports differing slightly between individual inspectors. In addition, the complete inspection of a part is a long and expensive operation.

The present invention is directed at a process permitting the tapping of complex parts in an automated manner, so as to provide a reliable, rapid and less costly uniform diagnosis than the existing inspection, whilst permitting an improved storage and presentation of the data and results.

According to the invention, this result is obtained by means of a tapping process for complex parts, according to which the part is subject to successive shocks on the basis of impacts distributed over the surface of the part to be inspected and from the acoustic response produced by these shocks is deduced a diagnosis relative to the presence of shallow faults, characterized in that sound signals produced by each shock are collected and at least two successive sound signals are compared in order to deduce therefrom in automated manner a fault diagnosis when a significant difference is detected between the successive sound signals.

The establishment of a diagnosis by the comparison of at least two successive sound signals collected during the inspection of the same part permits an automated inspection in a relatively short time. Thus, the inspection or testing of a part is independent of the specific characteristics of said part and its duration is virtually only determined by the mechanical constraints linked with the displacement of the tool used for applying the shocks and the acoustic constraints linked with the attenuation time of the sound signals induced by each of the shocks.

Preferably, application takes place to the part of calibrated, successive shocks, at a regulated frequency and in automated manner, based on impacts regularly distributed over the surface to be tested.

As a function of the particular case, the sound signals compared can either be consecutive signals produced by the shocks of adjacent impacts, or non-consecutive signals produced by the shocks of impacts separated by at least one intermediate impact.

In order to perform the process according to the invention, the conventional signal processing methods using either a comparison with a reference signal base, or an expert system have been avoided. Thus, a reference sound signal base is very difficult to form, in view of the great variety of such signals. Moreover, the blurred or unsharp character of sound signals, the presence of undesired noise and the difficulty of explaining what is heard by the ear have led to the avoiding of methods based on expert systems.

Therefore in a preferred embodiment of the invention, the successive sound signals are compared and from them an automatic diagnosis takes place with the aid of a neuron network or system.

Such neuron networks are described in greater detail in a manual entitled "Parallel Distributed Processing" by Rumelhart et al (particularly pp. 322–328, MIT Press, 1986).

Each neuron produces a weighted sum S of its inputs Ei and applies thereto a non-linear output function f using weighting coefficients Wi, called synaptic weights and the relation S=f(WiEi) is obtained.

These neurons are grouped in the form of a network, which is an array of neurons distributed over several layers, the outputs of each layer constituting the inputs of the following layer. The first layer of the network is called the input layer and the final layer the output layer, whereas the intermediate layers are known as hidden layers.

The resolution of a problem with the aid of a neuron network is broken down into three chronological phases:

A training phase: after fixing the architecture of the network this phase is performed with the aid of a set of representative examples of the problem to be solved. Each example is constituted by inputs relative to one case of the problem and the corresponding output or outputs (in the invention the inputs are representative values of two sound signals collected by a microphone placed in front of a part exposed to shocks and a single output indicates the presence or absence of faults). The training consists of determining the values of the synaptic weights such that, for each example, the network supplies a response close to the expected output or outputs. The training algorithm used is a gradient retropropagation algorithm like that described in the aforementioned manual (the retropropagation of the gradient of the error between the calculated output and the expected output). It is then hoped that on new cases, the network will supply an appropriate response (generalization capacity).

A validation phase: during this phase evaluation takes place of the response of the network to another set of representative examples of the problem to be solved, whose outputs are also known. The examples of said other set are different from those forming the set used for training.

An operating phase: during this phase, the synaptic weights determined during the training phase are used for issuing a diagnosis (the output values of the network are calculated on the basis of the input values as a function of the synaptic weights of the network).

Before comparing the successive sound signals with the aid of a neuron network, advantageously a preprocessing takes place on each of the sound signals in order to derive from the latter q representative values, q being a positive integer and use is made of the q representative values of at least two successive sound signals as input quantities of the neuron network.

In the preferred embodiment of the invention, each of the sound signals consisting of a sequence of m points, each determined by a time $t_i$ and by a signal amplitude $y_i$, the preprocessing consists of a stage of selecting, from among the sequence of m points, p representative points, and a smoothing stage during which the q representative values are deduced from the p representative points, m and p being integers such that m>p>q.

In this case, the selection stage consists of eliminating the points of the sequence of m points preceding the appearance of a first peak of the sound signal and of only retaining a given number p of points of the sequence of m points as from said first peak.

The smoothing stage consists of transforming the times $t_i$ of each of the p representative points into variables $\xi_i$ such that $\xi_i=(2 * t_i-\Delta t)/\Delta t$, in which $\Delta t$ represents the interval of the variations of the times $t_i$ and then determining by the method of least squares, the values of the parameters $a_n$ for which the expression $$S=\sum_i \left\{ y_i - \sum_n a_n TC_n(\xi_i) \right\}^2$$

is minimal, with n varying from 0 to N, $TC_n(\xi_i)$ being the degree N Chebyshev's polynomial, these values of the parameters $a_n$ being the q sought representative values.

In the preferred embodiment of the invention use is made of a four layer neuron network. This network has an input layer with x * q neurons, x being the number of successive sound signals compared, at least two hidden layers and an output layer having a single neuron.

In a particular architecture:
  the first hidden layer has an even number of neurons equal to half the number of neurons of the input layer, the neurons of the first hidden layer being distributed in equal numbers in a first and a second groups of neurons;
  all the neurons of the first group are connected to all the neurons of x groups of neurons of the input layer, each receiving a first half of the q representative values of one of the sound signals compared;
  all the neurons of the second group are connected to all the neurons of the x groups of neurons of the input layer, each receiving a second half of the q representative values of one of the compared sound signals.

In addition, the second hidden layer has a number of neurons exceeding 1 and below half the number of neurons of the first hidden layer and all the neurons of the second hidden layer are connected to all the neurons of the first hidden layer.

The invention is described in greater detail hereinafter relative to a non-limitative embodiment and the attached drawings, wherein show:

FIG. 1, very diagrammatically, an automated tapping apparatus for performing the process according to the invention.

Figure 2:
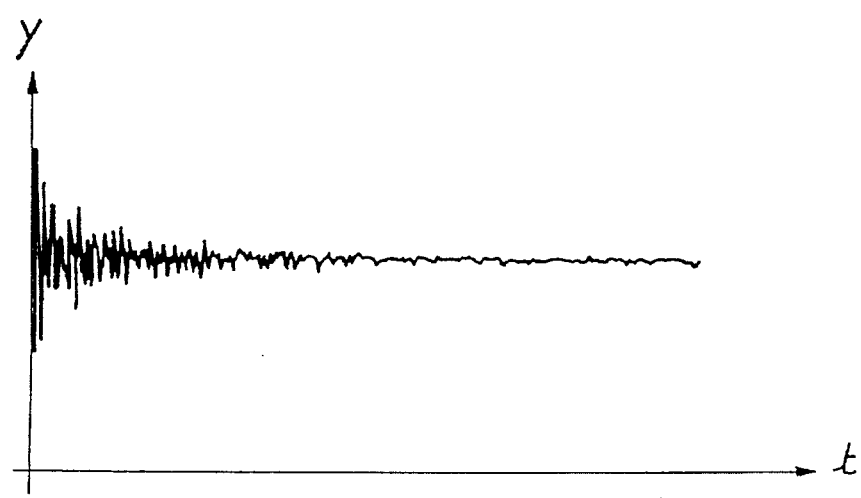

FIG. 2 a curve representing a rough sound signal detected by the apparatus of FIG. 1 after applying a shock to the part.

Figure 3:
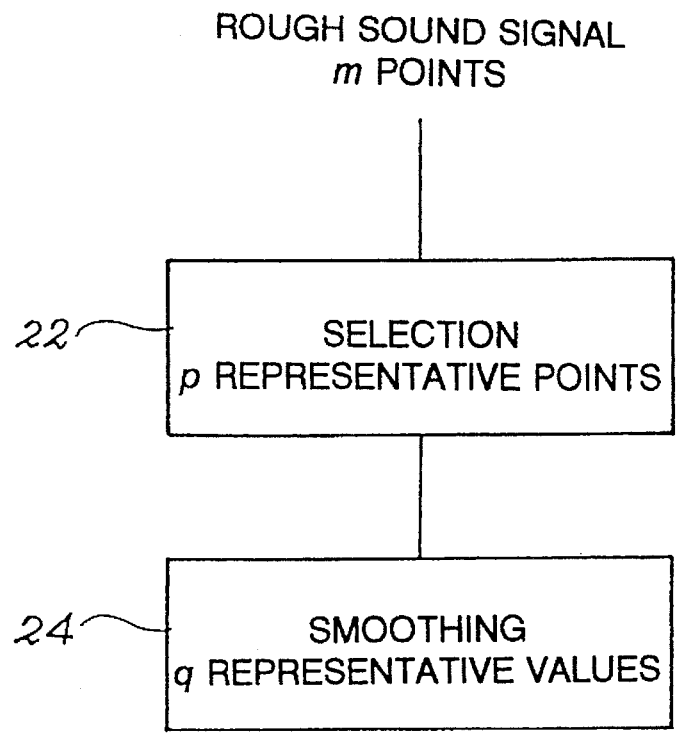

FIG. 3 a synaptic diagram representing the different preprocessing stages performed on each of the sound signals collected during the operation of the apparatus of FIG. 1.

Figure 4:
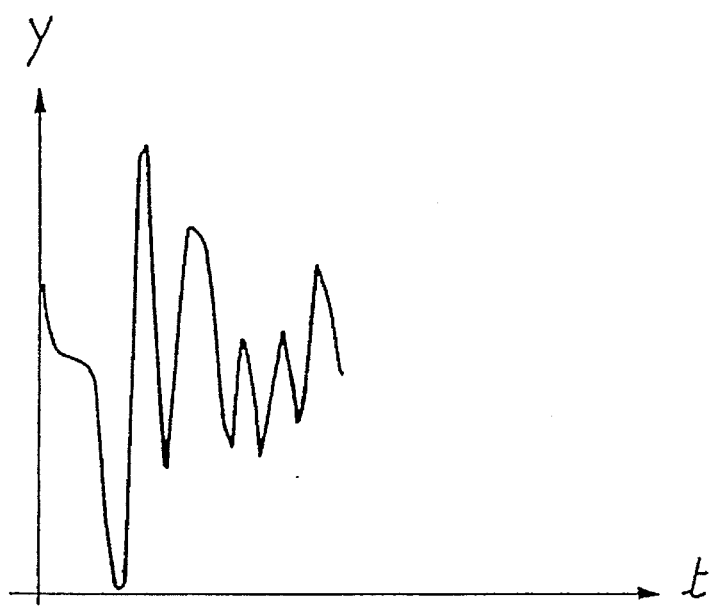

FIG. 4 a curve comparable to FIG. 2 representing a sound signal after a first selection stage of the preprocessing.

Figure 5:
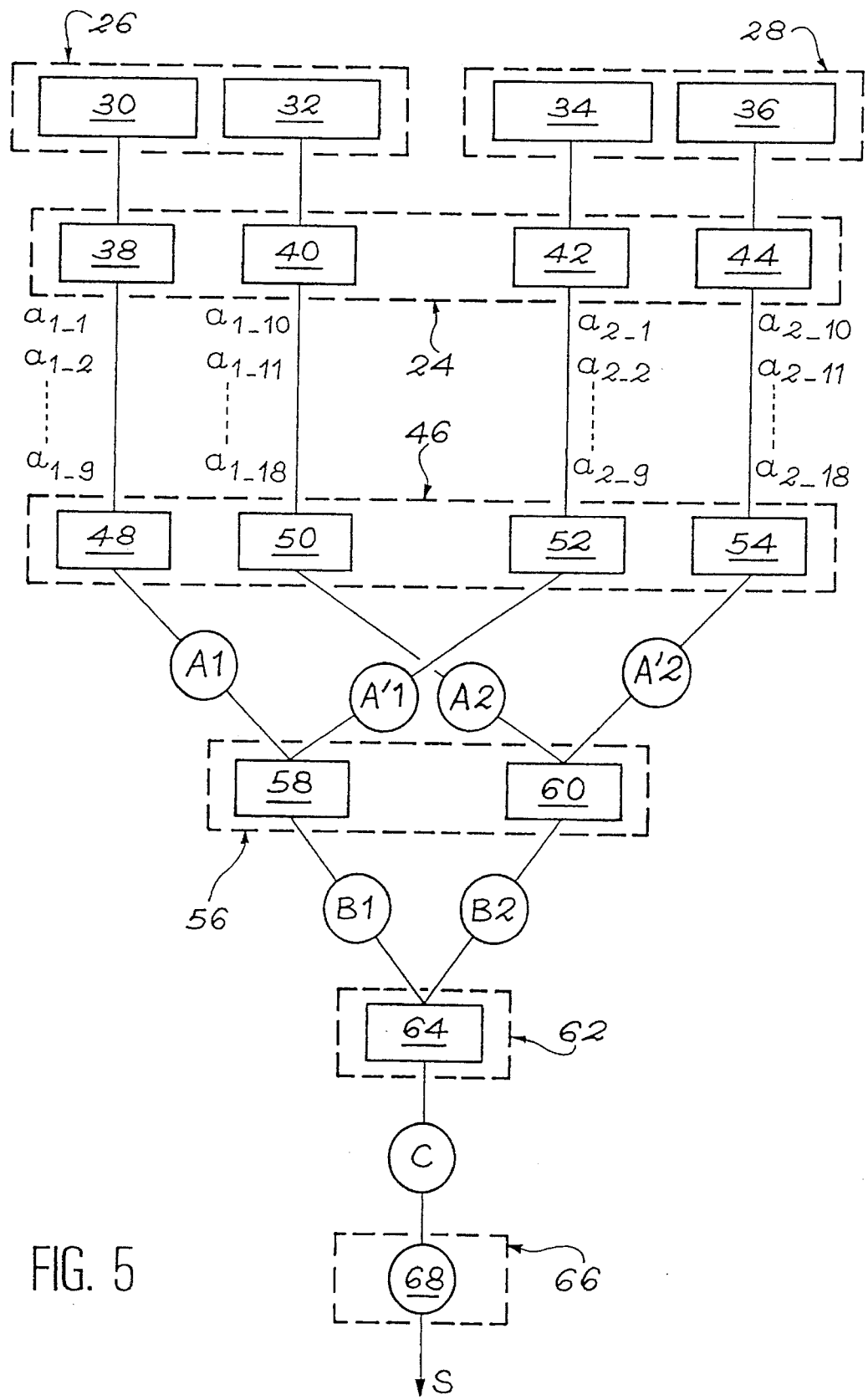

FIG. 5 a diagram representing in greater detail the end of the preprocessing and an example of the architecture of a neuron network used for comparing the representative values of two successive sound signals resulting from the preprocessing and establishing a fault diagnosis.

Figure 6A:
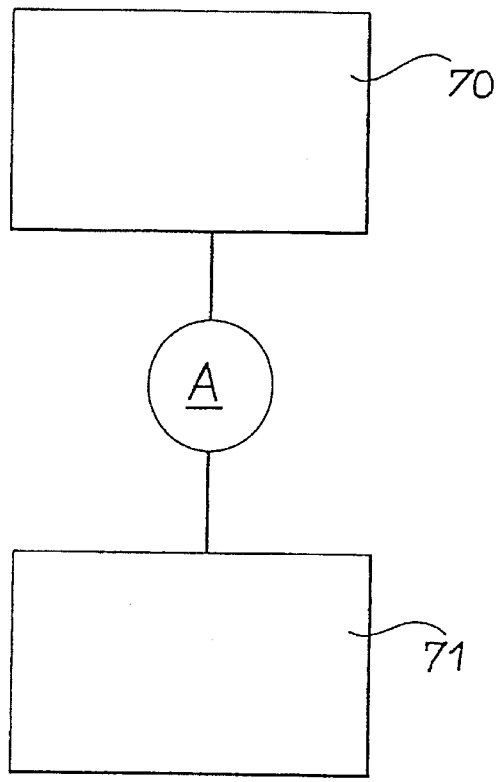
Figure 6B:
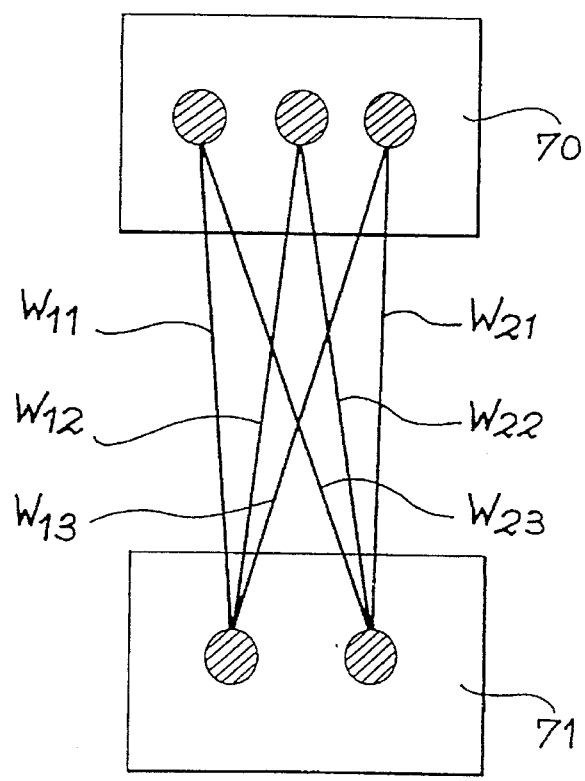

FIGS. 6A and 6B explain elements shown in FIG. 5.

In FIG. 1 the reference 10 designates a complex part, such as a helicopter blade, on which tapping is to take place.

To this end, the invention proposes an automated apparatus permitting on the one hand the application to the part 10 of successive shocks, whose impacts are regularly distributed over the surface to be tested and on the other the acquisition of sound signals representing the acoustic resonance produced by each shock and comparing between them at least two successive sound signals, in order to establish a fault diagnosis over the entire surface to be tested.

The shocks are applied to the part by an impacting head 12 installed on a support 13 able to travel in a plane substantially parallel to the mean plane of the surface to be tested, in two orthogonal directions X and Y.

The impacting head e.g. incorporates a steel hammer maintained by a solenoid counter to the action of a compression spring. The solenoid is excited or energized and deexcited or deenergized in automated manner at a regulated frequency, in such a way that calibrated shocks (in accordance with the stiffness of the spring) are applied by the hammer to the part under the action of the spring whenever the solenoid is deenergized.

Each new energizing of the solenoid leads to a raising of the hammer and is followed by a displacement of the impacting head 12 in accordance with a predetermined spacing and direction. The impacts of the different shocks are thus regularly distributed over the surface of the part, e.g. in accordance with a fine square matrix, whose spacing is preferably regulatable.

It should be noted that the impacting head can be implemented in any other appropriate manner. In particular, the magnetic control of the hammer can be replaced by a hydraulic or pneumatic control.

The control of the operation of the impacting head 12 and the synchronized control of its displacements are ensured by a control circuit 14, which can in particular be in accordance with that described in FR-A-2,062,069.

The automated apparatus diagrammatically illustrated in FIG. 1 also incorporates a microphone 16, which collects the sound signals representative of the acoustic resonance produced by each shock. Therefore the microphone 16 is mounted on the same support 13 as the impacting head 12 and in the immediate vicinity of the latter.

The microphone 16 is associated with an electronic acquisition circuit 18 for the sound signals. At the output of said electronic circuit 18 and as illustrated in FIG. 2, each of the rough sound signals consists of a curve giving the variations of the amplitude y of the signal, as a function of the time t. This curve is defined by a sequence of m points, m being a positive integer sufficiently high to supply a precise image of the signal in question. The number m of points defining each sound signal can in particular be equal to 1024 in the described embodiment. Each of the points of the sequence of m points is defined by a time $t_i$ and by an amplitude of the signal $y_i$, i being an integer varying between 1 and m. The total duration of each sound signal which corresponds to the time $t_m$ is e.g. 20 ms.

As is very diagrammatically illustrated by FIG. 1, each of the sound signals supplied by the electronic circuit 18 is transmitted to a management and control system 20, which is constituted by a microcomputer. Its main functions are the control of the testing sequence and the establishing of diagnoses leading to the obtaining of a cartography of the faults of the tested part. In addition, the control and management system 20 also regulates the acquisition parameters (matrix spacing, impact frequency, etc.), the acquisition of the data of the tested part (size of the surface to be tested) and the filing of the data and results.

To enable it to control the testing sequence, the management and control system 20 is connected to the control circuit 14 of the impacting head 12, as well as to not shown means permitting the control of the displacements of the support 13 carrying the impacting head 12 and the microphone 16.

In order to produce a diagnosis concerning the presence or absence of a fault at each impact, the management and control system 20, according to the invention, makes a comparison between at least two successive sound signals, which may or may not be consecutive. This comparison is performed by means of a neuron network. In view of the fact that the number of points representing each sound signal is much too high to be directly applicable to a neuron network, each sound signal undergoes a preprocessing beforehand, as is diagrammatically illustrated by the synaptic table of FIG. 3.

The first preprocessing stage consists of a selection stage from among the m points of each sound signal of p points representing said signal. It is based on the observation according to which the first part of each of the sound signals contains the majority of the informations necessary for the diagnosis. Thus, the sequence of the signal appears as echos of the first peak of said signal.

This selection stage, illustrated at 22 in FIG. 3, consists of a first zeroing phase during which the first points, which precede the appearance of the first signal peak, of very low amplitude y, correspond to a background noise.

A second phase of the selection stage 22 consists of only retaining a given number p of points of the sequence of m points, as from the appearance of the first peak. In the example described where each rough signal contains 1024 points, the number of representative points retained after said selection stage can e.g. be 32.

As is also illustrated in FIG. 3, the preprocessing consists of a second stage 24 during which q representative values are deducted from the p representative points of each sound signal. This number q of representative values, which is smaller than the number p of representative points is sufficiently low to be applicable to a neuron network at the same time as the q representative values of at least one other sound signal. In the case where the q representative values of two successive sound signals are applied to a neuron network, the number q of representative values of each sound signal, obtained after the second preprocessing stage 24, is e.g. equal to 18.

In the preferred embodiment described, the second preprocessing stage is a smoothing stage based on the use of Chebyshev's polynomials.

For a given variable $\xi$ in the range $[-1, 1]$, it is pointed out that the order n Chebyshev's polynomial designated $TC_n(\xi)$, is defined by the recurrence relation:

$$TC_n(\xi) = 2\xi Tc_{n-1}(\xi) - Tc_{n-2}(\xi),$$

with $Tc_o(\xi) = 1$
and $Tc_1(\xi) = \xi$

As each of the p representative points obtained after the selection stage 22 is determined by its amplitude $y_i$ and the time $t_i$ corresponding thereto, said instant or time $t_i$ varying in a variation range $\Delta t$ different from the range $[-1, 1]$ in which are defined the Chebyshev's polynomials, a change of variable must firstly be carried out to enable said polynomials to be used.

For each of the p representative points of a given sound signal, the time $t_i$ corresponding thereto is transformed into a new variable $\xi_i = (2* t_i - \Delta t)/\Delta t$. At this stage, each representative point of a given sound signal is consequently defined by the amplitude $y_i$ and by the variable $\xi_i$, representing the time corresponding to said amplitude.

On this new basis, the actual smoothing stage is then carried out. For this purpose, determination takes place by the method of least squares, of the values of the parameters $a_n$ for which the expression S is minimal, said expression S being defined by the relation:

$$S = \sum_i \left\{ y_i - \sum_n a_n Tc_n(\xi_i) \right\}^2,$$

with n varying from 0 to N and N representing the degree adopted for the Chebyshev's polynomial.

The degree N of the Chebyshev's polynomial is chosen so as to be sufficiently high to approach to the best possible extent the curve corresponding to the p representative points and is sufficiently low to ensure that the number of parameters $a_n$ is minimal. Thus, the values of the parameters $a_n$ are q sought representative values, whereof the number must be sufficiently low to be applicable to a neuron network, at the same time as the representative values of at least one other signal.

In order to facilitate the choice of the degree N of Chebyshev's polynomial, bearing in mind said latter observation, the smoothing stage 24 can be performed separately on at least two groups of representative points of a given sound signal. Thus, as is illustrated at the top of FIG. 5, in the case where the p representative points are subdivided into two groups, each of these groups is respectively formed by the p/2 first representative points and the p/2 last representative points.

More specifically, FIG. 5 shows the case where the number x of sound signals which are compared is 2. The reference 26 corresponds to the p representative points of the first signal S1 and the reference 28 to the p representative points of a second signal S2. The number p of representative points of each of the signals S1 and S2 can in particular be 32.

As indicated hereinbefore, the p representative points of each of the sound signals S1 and S2 are subdivided into a first group corresponding to the p/2 first points and a second group corresponding to the p/2 last points, so as to carry out a separate smoothing of each of these groups. In FIG. 5, the references 30 and 32 respectively designate the first and second groups of representative points of the first sound signal S1. In comparable manner, the references 34 and 36 respectively designate the first and second groups of representative points of the second sound signal S2. In the aforementioned example, each of the groups 30,32,34 and 36 consists of 16 representative points.

Each of the groups 30,32,34 and 36 of representative points is the object of a separate smoothing stage, designated respectively by the references 38,40,42 and 44 in FIG. 5. In exemplified manner, each of the separate smoothing stages is performed with a degree 8 Chebyshev's polynomial. The number of parameters $a_n$ and consequently the q/2 representative values obtained at the end of each of these four separate smoothing stages is then equal to 9.

The 9 representative values obtained at the end of the smoothing stage 38 from the 16 first representative points of the first signal S1 are designated by the references $a_{1-1}, a_{1-2}, \ldots, a_{1-9}$. The 9 representative values obtained at the end of the smoothing stage 40 from the 16 last representative points of the first signal S1 are designated by the references $a_{1-10}, a_{1-11}, \ldots, a_{1-18}$. The 9 representative values obtained at the end of the smoothing stage 42 from the 16 first representative points of the second signal S2 are designated by the references $a_{2-1}, a_{2-2}, \ldots, a_{2-9}$. Finally, the 9 representative values obtained at the end of the smoothing stage 44 from the 16 last representative points of the second signal S2 are designated by the references $a_{2-10}, a_{2-11}, \ldots, a_{2-18}$.

These four groups of 9 representative values obtained at the end of the smoothing stages 38,40,42 and 44 constitute the inputs of a neuron network, which is also shown in FIG. 5. The function of this neuron network is to compare several successive sound signals (two in the example shown), in order to produce a diagnosis concerning the presence or absence of faults in the surface region of the part in which shocks corresponding to the sound signals have been applied. The neuron network illustrated in FIG. 5 is a four layer network.

The input layer 46 of this neuron network consists of x * q neurons, x being the number of sound signals compared (two in the present example) and q being the number of representative values of each sound signal obtained after smoothing (18 in the example considered). In the considered example, the input layer consequently has 36 neurons.

In FIG. 5, the reference 48 designates a first block of 9 neurons belonging to the input layer 46. Each of these neurons receives one of the 9 representative values $a_{1-1}, a_{1-2}, \ldots, a_{1-9}$ of the first part of the first signal S1. Each of the 9 neurons of a second block 50 of the input layer receives one of the 9 representative values $a_{1-10}, a_{1-11}, \ldots, a_{1-18}$ of the second part of the first signal S1. The reference 52 designates a third block of 9 neurons belonging to the input layer, whereof each receives one of the 9 representative values $a_{2-1}, a_{2-2}, \ldots, a_{2-9}$ of the first part of the second signal S2. Finally, the input layer 46 also has a fourth block 54 of 9 neurons, whereof each receives one of the 9 representative values $a_{2-10}, a_{2-11}, \ldots, a_{2-18}$ of the second part of the second signal S2.

The second layer or first hidden layer 56 of the neuron network illustrated in exemplified manner in FIG. 5 consists of two blocks of 9 neurons each and respectively designated by the references 58 and 60.

The third layer or second hidden layer 62 of the neuron network is constituted by a block 64 of 5 neurons in the present example.

Finally, the fourth layer or output layer 66 of the neuron network illustrated in FIG. 5 consists of a single neuron 68, whose output supplies a diagnosis signal S. This diagnosis signal S, which e.g. varies between −1 and +1, makes it possible to conclude if a fault is present when the compared sound signals are considered to be different by the network, or that a fault is absent when the network concludes the quasi-identity of these sound signals.

The 9 neurons of the block 58 of the first hidden layer 56 are connected to the 9 neurons of the blocks 48 and 52 of the input layer of the network. The outputs of the neurons of the block 58 are consequently representative of the first part of each of the sound signals S1 and S2 which are compared.

In the same way, the 9 neurons of the block 60 of the first hidden layer 56 are connected to the 9 neurons of the blocks 50 and 54 of the input layer of the network. The outputs of the neurons of the block 60 are consequently representative of the second part of each of the two sound signals S1 and S2 compared by the network.

The 5 neurons of the block 64 forming the second hidden layer 64 are connected to the 9 neurons of each of the blocks 58 and 60 of the first hidden layer 56. Therefore the outputs of these 5 neurons are representative of all the sound signals S1 and S2 compared.

Finally, the neuron 68 forming the output layer 66 of the network is connected to each of the 5 neurons of the block 64 forming the second hidden layer 62.

In FIG. 5 is represented respectively by a single generic connection A1, A'1, A2, A'2, B1, B2 and C all the connections between the neurons of the blocks 48 and 58, 52 and 58, 50 and 60, 54 and 60, 58 and 64, 60 and 64, and 64 and 68.

In other words and as illustrated by FIGS. 6A and 6B, each of the generic connections A1, A'1, A2, A'2, B1, B2 and C corresponds in reality to a system of connections between the modules of the blocks to which these generic connections apply.

Thus, FIG. 6A shows in the form of a generic connection A all the connections illustrated in FIG. 6B between a group 70 comprising 3 neurons and a group 71 comprising 2 neurons. The values Wi are the synaptic weights allocated to each of the connections of FIG. 6B. Each generic connection, such as the connections A1, A'1, A2, A'2, B1, B2 and C in FIG. 5 consequently signifies that all the neurons of the first block are connected to all the neurons of the second block.

In the neuron network whose architecture has just been described relative to FIG. 5, each of the synaptic weights allocated to the different connections symbolized by the generic connections A1, A'1, A2, A'2, B1, B2 and C is determined once and for all prior to the operation of the network. This determination takes place by iteration with the aid of a retropropagation algorithm, on the basis of a first set of examples of which are known the inputs, as well as the expected output diagnoses. The thus determined synaptic weights are then validated with the aid of a second set of examples. The number of examples of each set is also as high as possible, e.g. between 1000 and 1500.

The validation tests have shown that the accuracy percentage of the diagnosis supplied by the neuron network is approximately 95. This percentage is very adequate when related to the detection of a defective surface area of a part. Thus, it makes it possible to locate the frontier of the faults with a good precision.

Advantageously, the diagnosis signals S supplied by the neuron network are displayed in cartography form on a graphic interface of the management and control system 20 (FIG. 1).

The architecture of the neuron network described hereinbefore with reference to FIG. 5 and based on a global approach to the problem only constitutes an example.

As a result of the inspection or testing process according to the invention, it consequently becomes possible to carry out an automated tapping of complex parts in a reliable and reproducible manner. Moreover, the duration and cost of the testing can be reduced compared with the presently used procedures and the results are displayed in a clear and accessible manner.

What is claimed is:

1. Process for tapping a complex part, wherein the part is subject to successive shocks based on impacts distributed over a surface to be tested of the part and a diagnosis relative to a presence of shallow faults is deduced from an acoustic response produced by said shocks, in which sound signals produced by each shock are collected and at least two successive sound signals are compared with one another in order to deduce therefrom in automated manner a fault diagnosis when a significant difference is detected between these successive sound signals.

2. Process according to claim 1, wherein calibrated, successive shocks are applied to the part at a regulated frequency and in an automated manner, on the basis of impacts regularly distributed over the surface to be tested.

3. Process according to claim 1, wherein consecutive sound signals produced by the shocks of adjacent impacts are compared.

4. Process according to claim 1, wherein non-consecutive sound signals produced by shocks of impacts separated by at least one intermediate impact are compared.

5. Process according to claim 1, wherein successive sound signals are compared and deduction takes place therefrom in automatic manner of a diagnosis with the aid of a neuron network.

6. Process according to claim 5, wherein q representative values are derived from each of the sound signals during a preprocessing step, q being a positive integer and wherein the q representative values derived from at least two successive sound signals are used as input data of the neuron network.

7. Process according to claim 6, wherein each of the sound signals consists of a sequence of m points, each determined by a time $t_i$ and by a signal amplitude $y_i$ so that the preprocessing consists of a selection stage from among the sequence of m points and p representative points, as well as a smoothing stage, during which the q representative values are deduced from the p representative points, m and p being integers such that m>p>q.

8. Process according to claim 7, wherein the selection stage consists of eliminating the points of the sequence of m points preceding the appearance of a first peak of the sound signal and of only retaining a given number p of points of the sequence of m points as from said first peak.

9. Process according to claim 7, wherein the smoothing stage consists of transforming the times $t_1$ of each of the p representative points into variables $\xi_i$ such that $\xi_i = (2* t_i - \Delta t)/\Delta t$, in which $\Delta t$ represents the interval of the variations of the times $t_i$, followed by the determination using the method of least squares of the values of the parameters a for which the expression $$S = \sum_i \left\{ y_i - \sum_n a_n Tc_n(\xi_i) \right\}^2$$

is minimal, with n varying from 0 to N, $Tc_n(\xi_i)$ being the degree N Chebyshev's polynomial, said values of parameters $a_n$ being the q sought representative values.

10. Process according to claim 6, wherein the neuron network comprises a four layer neuron network, including an input layer with x * q neurons, x being the number of successive sound signals compared, at least two hidden layers and an output layer having a single neuron.

11. Process according to claim 10, wherein the first hidden layer has an even number of neurons, equal to half the number of neurons of the input layer, the neurons of the first hidden layer being distributed in equal numbers in a first and a second group of neurons, all the neurons of the first group are connected to all the neurons of the x groups of neurons of the input layer, each receiving a first half of the q representative values of one of the compared sound signals and all the neurons of the second group are connected to all the neurons of x groups of neurons of the input layer, each receiving a second half of the q representative values of one of the compared sound signals.

12. Process according to claim 10, wherein the second hidden layer has a number of neurons exceeding 1 and lower than half the number of neurons of the first hidden layer and all the neurons of the second hidden layer are connected to all the neurons of the first hidden layer.

* * * * *